United States Patent [19]

Brantl et al.

[11] 4,390,527
[45] Jun. 28, 1983

[54] PHARMACOLOGICALLY ACTIVE PEPTIDES AND MEDICAMENTS CONTAINING THE SAME

[76] Inventors: Victor Brantl, Frauenplatz 10, 8000 München 2; Agnes Henschen, Am Klopferspitz, 8033 Martinsried; Hansjörg Teschemacher, Frankfurterstrasse 107, 6300 Giessen; Friedrich Lottspeich, Am Klopferspitz, 8033 Martinsried, all of Fed. Rep. of Germany

[21] Appl. No.: 258,617

[22] PCT Filed: Sep. 4, 1980

[86] PCT No.: PCT/DE80/00126
§ 371 Date: Apr. 29, 1981
§ 102(e) Date: Apr. 29, 1981

[87] PCT Pub. No.: WO81/00712
PCT Pub. Date: Mar. 19, 1981

Related U.S. Application Data

[63] Continuation-in-part of Ser. No. 229,577, Jan. 22, 1981.

[30] Foreign Application Priority Data

Sep. 6, 1979 [DE] Fed. Rep. of Germany ....... 2936099

[51] Int. Cl.$^3$ ................. A61K 37/00; C07C 103/52
[52] U.S. Cl. ................. 424/177; 260/112.5 R; 260/112.5 E
[58] Field of Search ................. 260/112.5 R, 112.5 E; 424/177

[56] References Cited

U.S. PATENT DOCUMENTS

| | | | |
|---|---|---|---|
| 4,123,523 | 10/1978 | Dutta et al. | 260/112.5 E |
| 4,127,534 | 11/1978 | Coy et al. | 260/112.5 E |
| 4,127,535 | 11/1978 | Coy et al. | 260/112.5 E |
| 4,223,020 | 9/1980 | Momany | 260/112.5 R |
| 4,223,021 | 9/1980 | Momany | 260/112.5 R |
| 4,226,857 | 10/1980 | Momany | 260/112.5 R |
| 4,228,155 | 10/1980 | Momany | 260/112.5 R |
| 4,228,157 | 10/1980 | Momany | 260/112.5 R |
| 4,228,158 | 10/1980 | Momany | 260/112.5 R |

*Primary Examiner*—Delbert R. Phillips
*Attorney, Agent, or Firm*—Merriam, Marshall & Bicknell

[57] ABSTRACT

Peptides of the formula Tyr$^1$-X-A-Pro-B-Pro-C . . . . . . . . , in which Tyr$^1$ is equal to the amino acid tyrosine and Pro is equal to the amino acid proline; A, B, C is any desired amino acid in the L-form and X any amino acid in the D-form; they act opiate-like and may be used as medicaments and animal medicaments.

7 Claims, No Drawings

PHARMACOLOGICALLY ACTIVE PEPTIDES AND MEDICAMENTS CONTAINING THE SAME

This application is a continuation-in-part of our co-pending patent application Ser. No. 229,577 filed Jan. 22, 1981, the entire contents of which is incorporated herein by reference.

The invention deals with new pharmacologically active peptides, in particular, peptides with opiate-like activity, methods for their synthetic manufacture, as well as pharmacologically active peptides manufactured according to these methods.

Pharmacologically active peptides have been known which display, in special biological testing systems, a specific opiate-like activity. They are, in particular, those penta-peptides isolated from the brain by Hughes et al. (Nature 258, 577, 1975): methionine cephalin and the leucine cephalin as well as their longer chain analogues. These known peptides and their synthetic derivatives have the disadvantage in that they lose their pharmacological activity, in this case an opiate-like activity, after treatment in vitro with proteases (for example, Pronase E. Merck) after a short incubation period. On in vivo administration, these peptides are easily attacked and destroyed by proteases naturally present in the body.

During a meeting of the Int. Narcotic Research Conference in June 1979 in North Falmouth, Mass., U.S.A., new peptides, $\beta$-casomorphins, have been described which display a novel sequence, which have, based on this sequence, a surprisingly increased stability to the proteases (for example: Pronase E. Merck). These peptides have a strong opiate-like activity in various known testing systems (receptor bonding test and isolated guinea pig intestine.) After injection of 0.35, $\mu$mole of $\beta$-casomorphin-5 (Tyr-Pro-Phe-Pro-Gly) into the ventricle system of the brain of rats, a strong opiate-like analgesia occurred which reached its maximum effectiveness within 10 minutes and completely disappeared after 60 minutes. This short duration of effectiveness as compared to morphine, with the same analgesia, hints at a possibly complete or partial decomposition of the substance by means of enzymes of the brain.

After parenteral or oral application of the substance, the $\beta$-casomorphin-5, which, by the way, has been known up to now as the peptide of the $\beta$-casomorphin family with the strongest opiate-like activity, does not show any analgetic effect. The dose in these tests amounted up to 150 mg per kg of body weight of the rats. This disadvantage of the known peptides can be partially or completely attributed to inactivation of the substance in the blood and/or the brain. Incubation tests of the substance with rat brain homogenate or blood plasma showed that the opiate-like activity disappears after a short incubation period of 15 minutes.

It is an object of the invention to provide new pharmacologically active peptides, $\beta$-casomorphins, analogues and/or derivatives, which, after incubation (up to 120 minutes) with rat brain homogenate and/or rat brain homogenate supernate and/or blood-plasma (see example of the embodiment) retain their pharmacological activity, for example, opiate-like. Furthermore, it is an object of the present invention to provide pharmacologically active peptides, $\beta$-casomorphins, analogues and/or derivatives which, after parenteral (for example, intravenous or subcutaneous injection) and/or oral application, show a pharmacological activity, in particular opiate-like. It is furthermore an object of the invention to make it possible for those skilled in the art, by means of disclosing the amino acid sequence, in particular, the position of the D-amino acid, to manufacture the peptide in any desired amount using customary methods.

These objects are satisfied according to the invention in that the pharmacologically active peptides have the following formula:

in which $Tyr^1$ is equal to the amino acid tyrosine and Pro is equal to the amino acid proline. A, B, C . . . can be any amino acid of the stereo chemical L-form. X can be any amino acid of the D-form.

According to a further development of the invention the pharmacologically active peptides have the following formulae:

$Tyr^1$-X-A
$Tyr^1$-X-A-Pro
$Tyr^1$-X-A-Pro-B
$Tyr^1$-X-A-Pro-B-Pro
$Tyr^1$-X-A-Pro-B-Pro-C
$Tyr^1$-X-A-Pro-B-Pro-C-Pro
$Tyr^1$-X-A-Pro-B-Pro-C-Pro-D . . .

A, B, C, D . . . can be any L-amino acid, including proline and tyrosine. X can be any desired D-amino acid.

According to another development of the invention the letters X, A, B, C, D of the listed peptides signify:

X: D-proline
A: L-phenylalanine
B: L-glycine
C: L-isoleucine
D: L-asparagine

According to a particularly advantageous further development of the invention X is replaced by the D-amino acids: D-alanine, D-threonine or D-valine.

According to another further development
(a) the end-positioned L-tyrosine of the general formula:

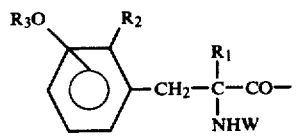

is substituted by:
$R_1$ for hydrogen or an alkyl group with 1 to 4 C-atoms
$R_2$ for hydrogen or together with $R_1$ for an ethylene bond,
$R_3$ for hydrogen, an alkyl group with 1 to 4 C-atoms or a $R_4CO$ group,
$R_4$ for a saturated or unsaturated straight or branched alkyl residue with 1 to 17 C-atoms, a phenyl residue or a phenyl-alkyl residue with 7 to 12 C-atoms, wherein the phenyl residues can be substituted by 1 or 2 substituents from the halogen series, alkyl with 1 to 4 C-atoms or alkoxy with 1 to 4 C-atoms, wherein the $R_3O$-group is in the meta position or para position to

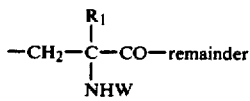

W for hydrogen, alkyl with 1 to 5 C-atoms, alkenyl with 3 to 5 C-atoms, cyclopropylmethyl, cyclobutylmethyl, R₄CO-, H-Lys-, H-Phe- or H-Tyr.

(b) the phenylalanine of the general formula:

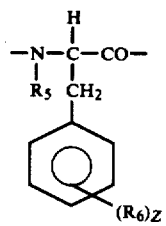

is substituted by:
R₅ for hydrogen of alkyl with 1 to 4 C-atoms,
R₆ for hydrogen, fluorine, chlorine, bromine, nitro, alkyl with 1 to 4 C-atoms or alkoxy with 1 to 4 C-atoms,
Z for 1 or 2 substituents.

(c) the L-proline (at the positions of the amino acids 4, 6, 8 . . . of the peptide) of the general formula:

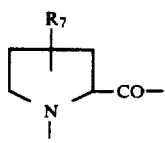

is so modified that:
R₇ for hydrogen, a hydroxy group, an alkyl group or an alkoxy group with 1 to 4 C-atoms,
that at the nitrogen, an alkyl group or alkoxy group with 1 to 4 C-atoms is attached,
that one or several keto groups are positioned in the ring.

(d) the end-positioned, C-terminal amino acid is an amide or an ester.

The increased stability of the peptides according to the invention to the decomposing enzymes is based on the introduction of a D-amino acid into the 2-position of the peptide. This introduction was completely far from our thoughts, since the discoverers and first scientists to describe this united class of β-casomorphins reported at the International Narcotic Research Conference in North Falmouth, Mass., U.S.A., in June 1979, that a completely surprising stability to the peptidases, for example, Pronase E. Merck, resulted from the alternating proline sequence. Thus it was completely far from our thoughts to undertake a further stabilization to protease cleavage. The D-amino acid in the 2-position of the peptide prevents decomposition by means of natural enzymes, since the natural enzymes preferably split peptide bonds among L-amino acids.

According to a further development of the invention the C-terminal amino acid of an odd numbered peptide is methionine. Particularly advantageous is the amino acid methionine in C-terminal-position on penta-peptides, hepta-peptides and nona-peptides. (The C-terminal amino acid is always located to the right of Tyr¹).

Very favorable is the derivative of methionine. The C-terminal methionine is present as —Met(O)—OH, for example:

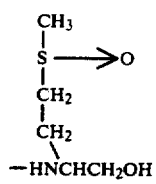

This derivative results in an improved opiate-like activity, that is to say, with smaller doses of peptides better results can be obtained.

According to a further development of the invention the pharmacologically active peptides according to the invention are synthesized by a method which is customary in peptide chemistry and/or in nature.

By customary methods we mean the introduction, as well as the splitting, of protective groups (for example, the protection of the amino group by means of carbobenzoxychloride; the protection of the acid groups as esters) during the synthesis. Also customary are syntheses on carrier substances, like, for example, polystyrene.

According to a further development of the invention the pharmacologically active peptides are created by bonding the peptide bond between the individual amino acids and/or the smaller peptide fragments by means of customary methods.

Human and animal medicaments are characterized in that they contain pharmacologically active peptides and/or their derivatives and/or their acid addition salts and/or their metal complexes as described in claims 1 to 10.

These acid addition salts can preferably be hydrochlorides, lactates or citrates. Zinc compounds, magnesium compounds, and cobalt compounds can be used as metal complexes. By derivatives we mean all compounds which have the peptide sequence of the L-amino acids with the introduction of a D-amino acid in the 2-position according to the invention as the basic structure and variations thereof which can be obtained by substituting or introducing individual groups. The positive or negative result on the respective desired effect can be simply ascertained by means of the respective tests.

These medicaments can be particularly used as antitussives, antidiarrhetics, analgetics, antipsychotics, and tranquilizers.

EXAMPLE

Synthesis of a penta-peptide according to the invention of the sequence:

Tyr-D-Ala-Phe-Pro-Gly-methylester and

Tyr-D-Pro-Phe-Pro-Gly-methylester

A. Synthesis Plan: The amino component is transformed at −15° C. or lower in dimethylformamide (DMF) with a 0.5 molar surplus of a mixed anhydride of a Z-amino acid-isobutylcarboxylic acid (wherein Z serves as a protective group and represents an N-benzyloxycarbonyl residue) in 2 to 4 hours.

The mixed anhydride is formed in DMF at −15° C. or lower in 10 to 15 min. by using a 6% surplus of Z-amino acid derivative and N-methylmorpholine via the chlorine formic acid-isobutyl ester system. The surplus of mixed anhydride is destroyed. At 0° C. the pH of the reaction product is set at 8 with an aqueous, saturated KHCO$_3$ solution and stirred for 30 min. at 0° C.

The peptides were extracted with ethyl acetate. The ethyl acetate-peptide mixture, in order to remove the Z-amino acid potassium salt, was washed three times with sodium chloride/water, and three times with water, and evaporated. The peptide which was thus obtained and which still carried the protective group Z, was hydrated in methanol. Then 100 to 500 mg of a Pd/activated carbon catalyst per mmol of peptide were added. The CO$_2$ splitting was controlled with a Ba(OH)$_2$ solution. The catalyst was filtered out (Schleicher & Schuell paper filter No. 595), washed extensively with water and the filtrate was evaporated on a rotary evaporator (Buechi, Rotavapor RE). The desired deblocked peptide is in the residue.

B. Synthesis of the penta-peptide:

Tyr-D-Ala-Phe-Pro-Gly-methylester and

Tyr-D-Pro-Phe-Pro-Gly-methylester

Step 1

(a) Manufacture of the mixed anhydride. (Z-Phe-Pro-mixed anhydride) 640 mg (1.6 mM; =6% surplus) of the dipeptide Z-L-Phe-L-Pro (wherein Z is a N-benzyloxycarbonyl residue, which acts as a protective group) are transformed in 20 ml of dimethylformamide (DMF) with 200 μl (1.5 mM) of chlorine-formic acid isobutyl ester at −15° C. after adding 170 μl (1.6 mM) of N-methylmorpholine, for 15 min.

(b) Preparation of the amino components 125.6 mg (1.0 mM) of glycine methyl ester hydrochloride are dissolved in 20 ml of DMF by adding 110 μl (1 mM) of N-methylmorpholine at −15° C.

Step 2

Conversion of the mixed anhydride of Step 1a with the amino component 1b. The Z-Phe-Pro-mixed anhydride is converted with the glycine methyl ester in 40 ml of DMF at −15° C. for 4 hours. Z-Phe-Pro-mixed anhydride +Gly-methester $$\xrightarrow[4 \text{ hr.}]{-15° \text{ C.}}$$

Z-Phe-Pro-Gly-metester.

Prior to processing, the 50% surplus of mixed anhydride is destroyed. At 0° C. the pH of the reaction product is brought to pH 8 with an aqueous saturated KHCO$_3$ solution and stirred for 30 min. at 0° C. After this the peptide is extracted with 50 to 100 ml of ethylacetate (EtAc), and the EtAc-peptide mixture is washed with a saturated aqueous sodium chloride solution. After a further final washing with water the EtAc-phase is evaporated.

Step 3

The protective group is split-off by hydration. The peptide is dissolved in 30 ml of methanol, and 100 mg of palladium on activated carbon (Merck) are added. After replacing the air with nitrogen, hydrogen is added to the reaction container. The hydrogenation is carried out at 25° C. to 30° C. The hydrogenation is finished when no CO$_2$ is released, that is, when after checking with an aqueous barium hydroxide solution, a precipitate is no longer formed. The solution is filtered, washed with water, and rotated in the rotary evaporator. This remaining intermediate product is then used in Step 4 as the amino component.

Step 4

(a) Manufacture of the mixed anhydride Z-D-Ala- and Z-D-Pro-mixed anhydride. 334.8 mg of Z-D-Ala (correspondingly also Z-D-Pro) are dissolved in 15 ml of DMF by adding 170 μl (1.5 mM) of N-methylmorpholine and converted with 180 μl (1.4 mM) of chlorine-formic acid-isobutyl ester at −15° C. in 15 min.

(b) Conversion of the mixed anhydride from Step 4a with the amino component of Step 3. Z-D-Pro or Z-D-Ala-anhydride+Phe-Pro-Gly-metester (in 15 ml DMF)

$$\xrightarrow[4 \text{ hr.}]{-15° \text{ C.}}$$

Z-D-Ala-Phe-Pro-Gly-methylester and

Z-D-Pro-Phe-Pro-Gly-methylester (The manufacture of the Z-D-Ala and of the Z-D-Pro is listed at the end of the synthesis.) The destruction of the excess mixed anhydride, the extraction steps, and the hydrogenation are carried out exactly as described before. The end product 4b serves as the amino component for Step 5. A check of the amino acid composition after the hydrolysis resulted in the correct molar amino acid relation of this peptide. A test of the opiate activity (testing method see Example I) did not result in any opiate-like activity.

Step 5

(a) Formation of the mixed anhydride (Z-Tyr-mixed anhydride). 629.24 (1.4 mM) of N,O-di-Z-L-tyrosine are dissolved in 15 ml of DMF by adding 165 μl (1.4 mM) of N-methyl-morpholine and converted with 175 μl (1.3 mM) of chlorine-formic acid-isobutyl ester at −15° C. in 15 minutes.

(b) Conversion of the mixed anhydride from Step 5a with the end product of Step 4b. The end product of Step 4b is dissolved in 15 ml of DMF and converted with the mixed anhydride of Step 5a at −15° C. in four hours. The destruction of the surplus mixed anhydride, the extraction and the hydrogenation take place as described above.

The subsequent splitting of the reaction products by means of gel filtration on a BIO-GEL P 2 column (Firma Biorad) <400 mesh, diameter 20 mm, length 1170 mm, flow speed 12 ml per hr, and ultra violet absorption measurement at 280 mm, and a fraction collector (each 20 min/frac) were carried out. All fractions of the gel filtration were tested with respect to their opiate-like activity using a longitudinal muscle plexus-myentericus preparation which had been suspended in an organ bath. For this test the individual fractions were evaporated under vacuum.

After putting the residues into water, portions of these samples were added to the organ bath and tested for their protecting effect on electrically stimulated contractions of the guinea pig intesting preparation. The restricting effect of the substances to be tested was considered as opiate-specific, when they were neutralized after adding the specific opiate-antagonist naloxon and when, after adding additional naloxon, no protection by the sample was any longer obtained. Preparation and electrical stimulation of the guinea pig intestine were carried through (frequency 0.1 hz, pulse 60 V, 0.5 ms) as described by Kosterlitz et al. (Kosterlitz, H. W.; Lydon, R. J.; and Watt, A. J., Brit. J. Pharmacol. 39, 398–413 (1970) and Schulz and Goldstein (Schulz, R.; and Goldstein, A. J.; Pharmacol. Exp. Ther. 183, 404–410 (1972).

The opiate-active fractions were dried.

An amino acid analysis of the opiate active fraction, carried out by means of an acid hydrolysis, resulted in a correct molar amino acid ratio corresponding to the two peptides D-Ala$^2$-$\beta$-casomorphin-5 and D-Pro$^2$-$\beta$-casomorphin-5.

We would like to point out that the activation of the opiate inactive tetrapeptide (Step 4b) by means of tyrosine bonding to an opiate-active peptide represents proof of a successful synthesis.

Manufacture of Z-D-Ala (Analogue of Z-D-Pro)

10 mM of D-Ala (891 mg), in 5 ml of 2 N NaOH, which have been ice-cooled and stirred vigorously, are treated with 3 ml of 50% chlorine formic acid benzyl ester in toluol and with 5.16 ml of 2 N NaOH.

The solution is acidified with 5.33 ml of 2 N HCl and extensively extracted with ethyl acetate. The split-off ethyl acetate phase is washed with HCl (diluted) and water and finally is extracted with a large amount of KHCO$_3$ solution. The combined aqueous extracts are brought up to pH 1.5 with HCl and extracted with ethyl acetate. The ethyl acetate phase then is again washed with diluted HCl. After another washing procedure with water, drying takes places via sodium sulphate. The solution is evaporated and the desired end product substance remains.

Proof of the stability of the opiate-like activity upon incubation with a rat brain homogenate of the D-Ala$^2$-$\beta$-casomorphin-5.

The brain and cerebellum of two decapitated rats (male, Sprague Dawley, weight 220 g) is immediately taken to an ice-cooled homogenizer (No. S 587, volume 35 ccm, Braun, Melsungen) which is filled with 7 ml of 0.05 M NaH$_2$PO$_4$ buffer. The homogenizing takes place at a rotational speed of 850 U/min while the homogenizer piston is moved up and down ten times. A small amount of the homogenate is taken out and stored on ice. The remainder is centrifuged at 5° C. for 15 min at 28,000×g. The homogenate of the centrifugation as well as the clear supernate after the centrifugation are used for the subsequent incubations.

All incubations of the substances with brain homogenate and brain-supernate take place at 37° C. The respective incubation time is terminated by heating for 10 min. at a temperature of 95° C. This heating up to 95° C. serves to destroy enzymes which are still present and which might be detrimental for the biological procedure for proving the opiate-like activity.

1–2 mg each of the $\beta$-casomorphin-5 and of the D-Ala$^2$-$\beta$-casomorphin-5 according to the invention are put into 50 $\mu$l of H$_2$O and mixed with 300 $\mu$l each of brain homogenate and brain-supernate. A sample of each is immediately heated from 37° C. up to 95° C. prior to the incubation. Thus these samples are in contact with the active enzymes only for a very short time and their content of opiate-like activity serves as a reference value at a zero point of time.

After 15, 30, 60, and 120 min. each, further samples of the two incubated opiates are taken from the incubator and heated up to 95° C.

The guinea pig intestine test described by Kosterlitz et al, supra serves as a proving system, which also includes the opiate amounts quantitatively.

A test with respect to the content of opiatic material in the individual containers showed that the containers which had been exposed to the enzymes for only a short time (zero value), had the same amount of activity for both of the opiates employed. However, after 30 minutes the containers, which contained the $\beta$-casomorphin-5, did not show any opiate-like activity any longer, while the strength of the opiate-like activity of the D-Ala$^2$-$\beta$-casomorphin-5 still could be proven after 30 minutes, as well as after 120 minutes, of incubation. Thus the peptide with the D-amino acid reveals a surprising stability to enzymes which split peptides.

An analeptic effect could be obtained with the D-Ala$^2$-casomorphins and the D-Pro$^2$-$\beta$-casomorphins during systematic application (intravenous and subcutaneous injection), which was not possible with the corresponding L-compounds. The dosage was higher, since it had a lower effect than morphine.

Analogously to the above-mentioned incubation example we tested the stability of the opiate-like activity towards blood plasma. Instead of 300 $\mu$l of homogenate, we employed 300 $\mu$l of freshly obtained rat blood plasma. It became obvious again that the $\beta$-casomorphin-5 without the D-amino acid was already destroyed after 30 minutes, while the D-Ala$^2$-$\beta$-casomorphin-5 retained its full activity.

The medicaments and animal medicaments according to the invention are pharmaceutical preparations which contain, besides their non-toxic, inert, pharmaceutically acceptable carrier substances, one or several substances according to the invention, or which consist of one or several effective substances according to the invention.

Pharmaceutical preparations in dosage units also belong to the present invention. That means that the preparations in the form of individual parts, for example, pellets, dragees, capsules, pills, suppositories and vials are provided, the effective substance content of which corresponds to a fraction or a multiple of an individual dose. The dosage units, for example, may contain 1, 2, 3 or 4 individual doses or ½, ⅓, or ¼ of an individual dose. An individual dose preferably contains the amount of effective substance which is given during one administration and which usually corresponds to a full, a half, or a third, or a fourth of a daily dose.

By non-toxic, inert, pharmaceutically acceptable carrier substances is meant the solid, semi-solid, or liquid diluents, fillers, and formulating adjuvants of any kind.

We would like to name pellets, dragees, capsules, pills, granulates, suppositories, solutions, suspensions and emulsions, pastes, salves, jelly, creams, lotions, powders and sprays as preferred pharmaceutical preparations.

Pellets, dragees, capsules, pills, and granulates may contain the effective substance/s, besides the usual carrier substances, such as fillers and extender means (for example: starches, milk sugar, cane sugar, glucose, mannitol and silicic acid), binders (for example: carboxymethylcellulose, alginate, gelatin, polyvinylpyrrolidone), moisture preserving means (for example: glycerine), disintegrating agents (for example: agar-agar, calcium carbonate and sodium bicarbonate), solution inhibitors (for example: paraffin) and resorption accelerators (for example: quarternary ammonium compounds), adsorption means (for example: kaolin and bentonite) and lubricants (for example: talcum, calcium stearate and magnesium stearate and solid polyethylene glycols) or mixtures of the named substances.

The pellets, dragees, capsules, pills, and granulates may be provided with the customary coatings and covers possibly containing opacifying means and also they may be so formed that they release the effective substance/s only or preferably in a certain area of the intestinal tract, possibly slowly for which, for example, polymer substances or waxes may be used as imbedding masses.

The effective substance/s may possibly be available in one or several of the above-mentioned carrier substances in micro capsules in order to obtain a delaying action.

Suppositories, in addition to the effective substance/s, may contain the customary water soluble or water insoluble carrier substances, for example: polyethylene glycols, fats, for example: cacao fat and higher esters (for example, $C_{14}$-alcohol with $C_{16}$-fatty acid) or other mixtures of these substances.

Salves, pastes, creams, and jellies may contain, besides the effective substance/s, the customary carrier substances (for example: animal and vegetable fats, waxes, paraffins, starches, gum tragacanth) or mixtures of these substances.

Solutions and emulsions may contain, besides the effective substance/s, the customary carrier substances such as solubilizing means, agents imparting solution, and emulsifying agents; for example, water, ethyl alcohol, isopropyl alcohol, ethyl carbonate, ethyl acetate, benzyl alcohol, benzyl benzoate, propylene glycol, oils, in particular, cottonseed oil, peanut oil, corn oil, olive oil, and sesame oil, glycerine, polyethylene glycols, or mixtures of these substances.

The solutions and emulsions also may be available in sterile and blood isotonic form for parenteral application.

Suspensions may contain, besides the effective substance/s, the customary carrier substances like liquid diluents, (for example: water, ethyl alcohol, propylene glycol), suspending means (for example: ethoxylated isostearyl alcohols, polyoxyethylene sorbitan esters, and sorbitan esters, microcrystalline cellulose) or mixtures of these substances.

The named formulations may also contain coloring agents, preserving agents, as well as additives improving smell and taste, for example: peppermint oil and eucalyptus oil; and sweetening agents, for example: saccharin.

The therapeutically effective compounds are preferably present in the above named pharmaceutical preparations in a concentration of approximately 0.1 to 99.5, preferably of about 0.5 to 95 weight percent of the entire mixture.

The above-named pharmaceutical preparations may contain, besides the effective substances according to the invention, also additional pharmaceutically effective substances.

The manufacture of the above-named pharmaceutical preparations is accomplished in a conventional manner according to known methods, for example, by mixing the effective substance/s with the carrier substance/s.

The effective substances or the pharmaceutical preparations may be applied locally, orally, parenterally, intraperitoneally, and/or rectally, preferably parenterally.

In general, it is considered to be of advantage, with respect to human medicaments, to administer the effective substance/s according to the invention in total amounts of about 5 to 500, preferably 50 to 250, mg every 24 hrs, preferably in the form of several individual doses in order to obtain the desired results. An individual dose preferably contains the effective substance/s according to the invention, in an amount of about 10 to about 300, in particular 50 to 200, mg/dose. However, it may be necessary to vary from the stated doses, that is, depending on the body weight of the subject to be treated, the type and seriousness of the sickness, the type of preparation, and the administration of the medicament, as well as the period of time of the interval, within which the medicament is given. Thus it may be sufficient in some cases to use less than the above-named amounts of effective substance/s while in other cases the above-mentioned amount of effective substance must be exceeded.

The determination of the respective necessary maximum doses and type of application of the effective substances can be easily accomplished by those skilled in the art based on their expert knowledge.

We claim:

1. Pharmacologically active peptides of the following formulas:

$Tyr^1$-X-A,
   $Tyr^1$X-A-Pro,
   $Tyr^1$-X-A-Pro-B,
   $Tyr^1$-X-A-Pro-B-Pro,
   $Tyr^1$-X-A-Pro-B-Pro-C,
   $Tyr^1$-X-A-Pro-B-Pro-C-Pro and
   $Tyr^1$-X-A-Pro-B-Pro-C-Pro-D wherein X represents D-proline, D-alanine, D-threonine or D-valine; A represents phenylalanine, proline and tyrosine B represents L-glycine, proline and tyrosine, C represents L-isoleucine and D represents L-asparagine, proline and isoleucine.

2. $D-Ala^2-\beta$-casomorphin-5
3. $D-Pro^2-\beta$-casomorphin-5
4. Pharmacologically active peptides according to claim 1 in which:
   (a) the end-positioned L-tyrosine present is of the general formula

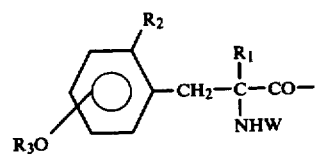

wherein the individual meaning is:
$R_1$ for hydrogen or an alkyl group with 1 to 4 C-atoms, $R_2$ for hydrogen or together with $R_1$ for an ethylene bond, $R_3$ for hydrogen, an alkyl group with 1 to 4 C-atoms or a $R_4CO$-group, $R_4$ for a saturated or unsaturated straight or branched chain alkyl residue with 1 to 17 C-atoms, a phenyl residue or a phenylalkyl residue with 7 to 12 C-atoms, in which the phenyl residues can be substituted by 1 or 2 substituents of the halogen series, alkyl with 1 to 4 C-atoms or alkoxy with 1 to 4 C-atoms, in which the $R_3O$ group is in meta or para position to

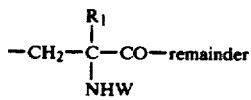

W represents hydrogen, alkyl with 1 to 5 C-atoms, alkenyl with 3 to 5 C-atoms, cyclopropylmethyl, cyclobutylmethyl, $R_4CO$—, H—Arg—, H—Lys—, H—Phe—, or H—Tyr—, (b) the L-phenylalanine is of the general formula

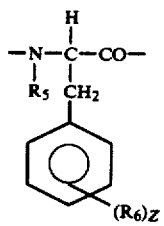

in which:

$R_5$ represents hydrogen or alkyl with 1 to 4 C-atoms, $R_6$ represents hydrogen, fluorine, chlorine, bromine, nitro, alkyl with 1 to 4 C-atoms or alkoxy with 1 to 4 C-atoms, Z for 1 or 2.

(c) the L-proline (at the 4, 6 or 8 positions of the peptide) have the formula

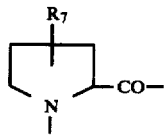

in which:

$R_7$ represents hydrogen, a hydroxy group, an alkyl group or alkoxy group with 1 to 4 C-atoms; an alkyl group or alkoxy group with 1 to 4 C-atoms is bonded at the nitrogen, and one or more keto groups are positioned on the ring; and (d) the end-positioned, C-terminal amino acid positioned to the right of Tyr in the peptide chain is present as an amide or ester.

5. A pharmacologically active peptide according to claim 1 in which the peptide has an end positioned methionine and the peptide is a tri-, penta-, hepta- or nonapeptide.

6. A pharmaceutical composition comprising a non-toxic pharmaceutically acceptable carrier and a peptide according to claim 1, or an acid addition salt or metal complex of the peptide, with said peptide constituting about 0.1 to 99.5 weight percent of the composition.

7. A pharmaceutical composition in unit dosage form comprising a non-toxic pharmaceutically acceptable carrier and about 10 to 300 mg of a peptide according to claim 1, or an acid addition salt or metal complex of the peptide.

* * * * *